United States Patent [19]

Stanko et al.

[11] Patent Number: 5,801,198

[45] Date of Patent: Sep. 1, 1998

[54] RETARDING NEUTROPHIL INFILTRATION AD MORPHOLOGIC REDUCTION IN ISCHEMIC BOWEL TISSUES

[75] Inventors: Ronald Thomas Stanko, Pittsburgh, Pa.; Robert Harold Miller; Mark Anthony McCamish, both of Worthington, Ohio

[73] Assignees: University of Pittsburgh Medical Center, Pittsburgh, Pa.; Abbott Laboratories, Abbott Park, Ill.

[21] Appl. No.: 502,024

[22] Filed: Jul. 13, 1995

[51] Int. Cl.$^6$ .................................................. A61K 31/195
[52] U.S. Cl. .............................. 514/563; 514/3; 514/557; 514/625
[58] Field of Search .................................. 514/563, 425, 514/3, 557

[56] References Cited

U.S. PATENT DOCUMENTS

| | | | |
|---|---|---|---|
| 4,158,057 | 6/1979 | Stanko | 424/252 |
| 4,351,835 | 9/1982 | Stanko | 424/252 |
| 4,415,576 | 11/1983 | Stanko | 424/252 |
| 4,548,937 | 10/1985 | Stanko | 514/251 |
| 4,812,479 | 3/1989 | Stanko | 514/557 |
| 4,874,790 | 10/1989 | Stanko | 514/557 |
| 5,134,162 | 7/1992 | Stanko | 514/557 |
| 5,256,697 | 10/1993 | Miller et al. | 514/625 |
| 5,283,260 | 2/1994 | Miller et al. | 514/563 |
| 5,294,641 | 3/1994 | Stanko | 514/540 |
| 5,395,822 | 3/1995 | Izumi et al. | 514/3 |
| 5,480,909 | 1/1996 | Stanko | 514/557 |
| 5,508,308 | 4/1996 | Miller et al. | 514/563 |

FOREIGN PATENT DOCUMENTS

WO 93/21147  10/1993  WIPO.

OTHER PUBLICATIONS

Stanko, et al., Pyruvate Inhibits Clofibrate–Induced Hepatic Peroxisomal Proliferation and Free Radical Production in Rats. *Metabolism*, vol. 44:2, Feb. 1995, pp. 166–171.

Cicalese, et al., Pyruvate Prevents Ischemia–Reperfusion Mucosal Injury of Rat Small Intestine. *The American Journal of Surgery*, vol. 171, Jan. 1996, pp. 97–101.

DeBoer, et al., Pyruvate enhanes recovery of rat hearts after ischemia and reperfusion by preventing free radical generation. *The American Physiological Society*, pp. H1571–H1576.

Rigobello et al., Effect of pyrovate on rat heart thiol status during ischemia acl hypoxia followed by reperfusion. (1993) (see abstract).

Simmonds, N.J. et al., Gastro Enterology 103:186–196, 1992 "Chemiluminescence Assay of Mucosal Reactive Oxygen Metabolites in Inflammatory Bowel Disease".

Borg, D., "Oxygen Free Radicals & Tissue Injury" in Oxygen Free Radicals in Tissue Damage (Tarr et al., eds.) Birkhauser, Boston 1993.

*Primary Examiner*—Kevin E. Weddington
*Attorney, Agent, or Firm*—Donald O. Nickey; Thomas D. Brainard

[57] ABSTRACT

Treating mammals having ischemic bowel with a therapeutic quantity of pyruvate enterally or parenterally will retard neutrophil infiltration and retain morphology during and following the bowel ischemia. The pyruvate is introduced into the patient enterally or parenterally during the bowel ischemia or the succeeding bowel reperfusion and, preferably, prior to the bowel ischemia. The pyruvate dosage is from 1% to 20% by weight of the patient's caloric intake.

14 Claims, 2 Drawing Sheets

RETARDING NEUTROPHIL INFILTRATION AD MORPHOLOGIC REDUCTION IN ISCHEMIC BOWEL TISSUES

BACKGROUND OF THE INVENTION

1. Field of the Invention

The invention concerns treatment of mammals to retard ischemic bowel disease. Bowel ischemia and reperfusion is commonly associated with a sudden increase of generated free-radicals, accompanying neutrophil infiltration and accompanying cell death or loss of morphology which may result in the death of the mammal. Ischemia refers to the stoppage of blood flow to a particular organ or muscle. Reperfusion refers to the restoration of blood flow to the affected organ or muscle.

According to the present invention, providing the mammal with pyruvate prior to, and/or during the onset of bowel ischemia will significantly inhibit the neutrophil infiltration to the affected bowel. During reperfusion of the ischemic bowel, the presence of pyruvate in the bowel will significantly retard neutrophil infiltration and villi deterioration.

2. Description of the Prior Art

Pyruvate has a number of useful applications in medical treatment. Pyruvate has been described for retarding fatty deposits in livers (U.S. Pat. No. 4,158,057); for diabetes treatment (U.S. Pat. No. 4,874,790); for retarding weight gain (U.S. Pat. Nos. 4,812,879, 4,548,937, 4,351,835); to increase body protein concentration in a mammal (U.S. Pat. No. 4,415,576); for treating cardiac patients to increase the cardiac output without accompanying increase in cardiac oxygen demand (U.S. Pat. No. 5,294,641); for extending athletic endurance (U.S. Pat. No. 4,315,835); for retarding cholesterol increase (U.S. Pat. No. 5,134,162); for inhibiting growth and spread of malignancy and retarding DNA breaks (application Ser. No. 08/194,857, filed Feb. 14, 1994); and for inhibiting generation of free radicals (application Ser. No. 08/286,946 filed Aug. 8, 1994). Pyruvate in various forms has been proposed for enteral administration and for parenteral administration. Typically pyruvates are available in the form of salts, e.g., calcium pyruvate and sodium pyruvate; pyruvate analogs of amino acids, e.g. pyruvyl-amino acids such as pyruvyl-glycine, pyruvyl-alanine, pyruvyl-leucine, pyruvyl-valine, pyruvyl-isoleucine, pyruvyl-phenyl-alanine, pyruvyl-proline, and their amides. See U.S. Pat. Nos. 5,283,260 and 5,256,697 for pyruvyl-amino acids.

Pyruvate may be administered to a mammal enterally or parenterally to super physiologic levels in the mammal. The amount of administered pyruvate preferably is from 1 to 20 per cent of the mammal's caloric intake. For enteral dosage, the pyruvate may be dispersed or dissolved in a beverage product or may be included in cookies, candies or other foods. The pyruvate may be introduced as an aqueous solution parenterally. A preferred administration procedure is an aqueous energy maintenance drip which includes not only sugars but also the selected pyruvate or pyruvates. See U.S. patent application Ser. No. 08/286,946 filed Aug. 8, 1994. Regardless of the administration procedure, according to this invention, the presence of super physiological pyruvate in a mammalian bowel or circulatory system will retard development of free-radicals during an ischemia incident in the mammal's bowel and during reperfusion.

DESCRIPTION OF THE PREFERRED EMBODIMENTS

Figure 1:
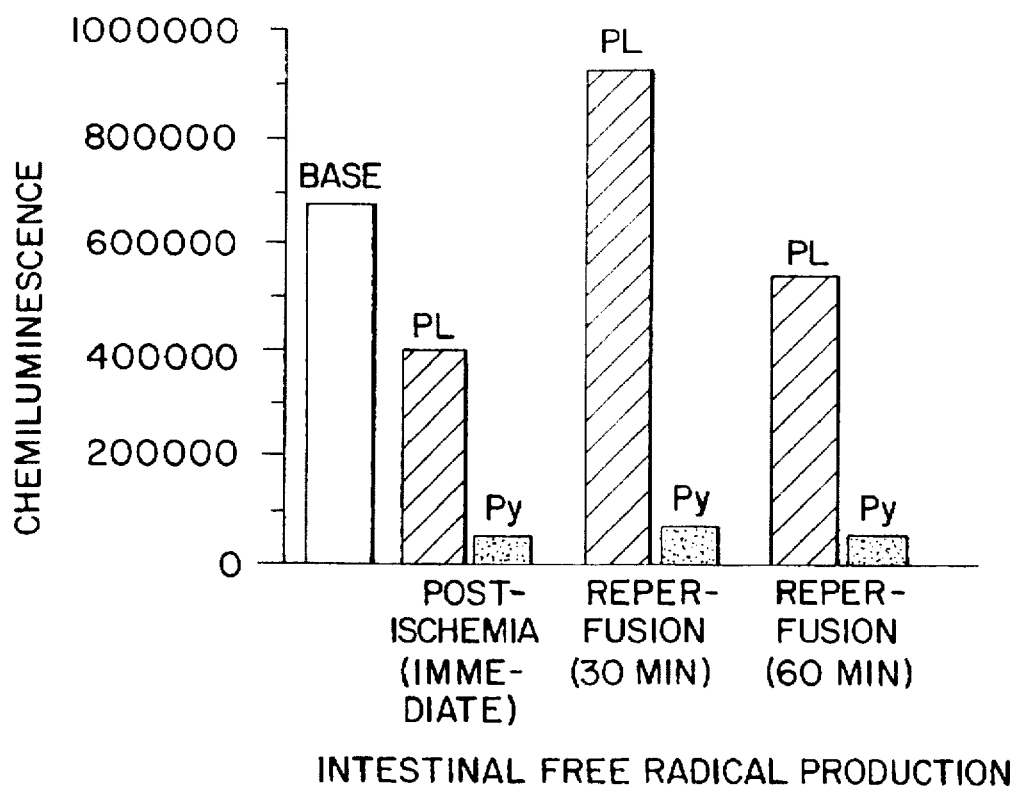
FIG. 1 is a graphical representation of the measured chemiluminescence resulting from intestinal free-radical generation during ischemia and subsequent reperfusion, comparing a placebo (PL), a pyruvate (PY) treatment and a base line condition.

Ischemia is a condition in which the flow of blood has been interrupted to a particular region of the mammal anatomy, e.g., muscles or organs. Bowel ischemia is commonly encountered in the course of surgery, mechanical accidents, and intestinal disorders.

Restoration of the flow of blood to the ischemic anatomy is called reperfusion. At the onset of bowel reperfusion a sudden increase of free-radicals is identified. The free-radical production of the mammal remains high for extended periods, e.g., one to two hours following onset of reperfusion. The high level of free-radicals usually causes irreversible damage to the affected anatomy. The elevated free-radical production in the bowel results in cell necrosis (cell death), a decreased morphology and death of the mammal. See "Oxygen Free Radicals in Tissue Damage" Merrill Tarr et al, Birkhauser Boston, 1933. Morphology is the form and structure of the mammal.

A patient, treated with pyruvate prior to the onset of bowel ischemia will not display the elevated free-radical development, but instead will maintain free-radical development at a level which is normal or lower than base line level, throughout the ischemia and subsequent reperfusion. The neutrophil infiltration is retarded and the morphology is retained.

EXAMPLE 1

The small intestine of each of six laboratory rats was tied to closure. The bowel downstream from the closure received directly for ten minutes before and during treatment either:

PLACEBO (PL) a liquid diet preparation containing aqueous polyglucose; or

PYRUVATE (PY) a liquid diet preparation containing aqueous polyglucose with 10% of the energy (caloric) content of the polyglucose being displaced by a mixture of sodium and calcium pyruvate constituting 10% (by energy) of the liquid diet, i.e., 10% of the caloric intake.

The superior mesenteric artery which supplies blood to the intestines was occluded in each of the six laboratory rats to cause bowel ischemia. The ischemia continued for 45 minutes at which time the mesenteric artery occlusion was released and reperfusion of the affected bowel commenced.

A portion of the intestine of each laboratory rat was removed:

(A) Immediately following ischemia;

(B) After 30 minutes reperfusion;

(C) After 60 minutes reperfusion.

Each intestine portion was analyzed for free radicals by chemiluminescence (measured in intensity/mg protein) and examined by light microscopy. Chemiluminescence measurements are described by Simmonds, N.J. et al, GASTROENTEROLOGY 1992, Vol 103, Pages 186–196.

The baseline chemiluminescence value for the rats was obtained prior to the testing at 684,000±68,200 chemiluminescence units, a direct correlation to the free-radical population. The values for the Placebo (PL) and for the Pyruvate (PY) treatment are indicated in TABLE I and graphically presented in FIG. 1.

TABLE I

FREE-RADICAL CONTENT OF INTESTINE OF
LABORATORY RATS FOLLOWING BOWEL ISCHEMIA
(Measured in chemiluminescence units)

|  | PLACEBO | PYRUVATE TREATMENT |
| --- | --- | --- |
| Post Ischemia (Immediate) | 409,000 ± 76,200 | 59,700 ± 10,400 |
| Reperfusion (30 minutes) | 933,000 ± 298,000 | 69,800 ± 20,400 |
| Reperfusion (60 minutes) | 543,000 ± 309,000 | 62,200 ± 15,900 |

The significant reduction of free-radicals (as measured by chemiluminescence) resulting from Pyruvate treatment (PY) of the mammal is illustrated in FIG. 1 wherein the vertical cross-hatch areas representing Pyruvate treatment (PY) are significantly lower than the horizontal cross-hatch areas representing the Placebo (PL). The reduction is apparent at the end of the ischemia and throughout the observed reperfusion.

The placebo intestine segment, after reperfusion, was discolored and appeared necrotic. All of the placebo segments displayed petechiae (small hemorrhagic spots) while the pyruvate segments did not show petechiae.

In further tests, with bowel ischemia for 30 minutes followed by reperfusion for 30 minutes, laboratory rats were fed as described in EXAMPLE 1. The placebo rats had the described standard diet. The pyruvate treatment rats had the pyruvate-modified standard diet (A) Prior to and during the ischemia; or (B) Only after the onset of the ischemia.

Figure 2:
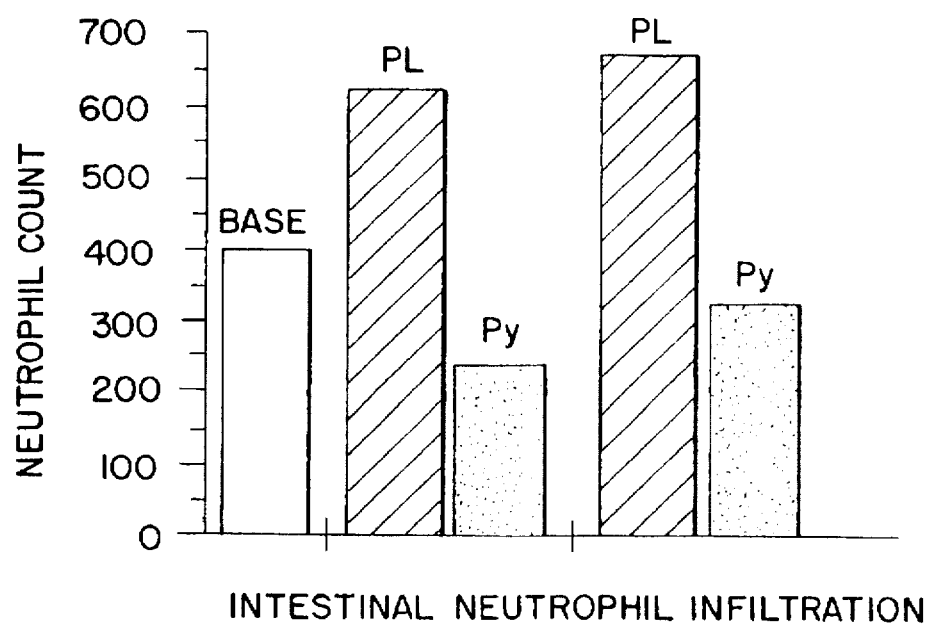
FIG. 2 is graphical representation of the neutrophil count for two mammals, one of which has received pyruvate (PY) treatment and the other of which is a placebo (PL). These are compared to a base line condition, prior to the ischemia onset. The neutrophil count was made at 30 minutes reperfusion following bowel ischemia.

The neutrophil infiltration of the intestine was measured and graphed on FIG. 2. The baseline condition in FIG. 2 indicates the population of neutrophil in the intestine prior to any evaluations. The two bars labeled indicate the neutrophil population at the end of 30 minutes reperfusion following 30 minutes ischemia.

(A) Where pyruvate had been introduced into the rat prior to the onset of ischemia the neutrophil infiltration (PY) was reduced below the base condition, whereas the placebo (PL) showed increased neutrophil infiltration.

(B) Where the pyruvate diet was commenced immediately following the onset of ischemia, similar results are observed.

From FIG. 2 it appears that the pyruvate is beneficial in retarding neutrophil infiltration in both situations i.e., when supplied prior to and during the ischemia and also when supplied only after onset of the ischemia or the onset of reperfusion.

For visual evidence of the effect of ischemia on intestines, two laboratory rats were evaluated. One rat, PL, received the described standard diet and the other rat, PY, received the described pyruvate modified standard diet. The superior mesenteric arteries of both rats were blocked to create bowel ischemia for 60 minutes.

Figure 3A:
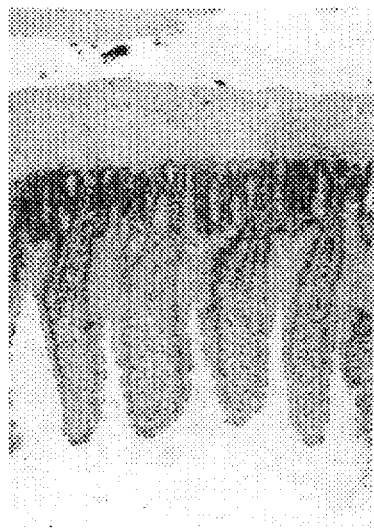
FIG. 3 includes three microphotographs showing intestinal villi under different conditions.

At the end of the 60 minutes of reperfusion, the rats were sacrificed and microphotographs were obtained of a cross-section through the small intestine, which is covered with small villi, extending into the interior of the intestine from the muscle wall. These microphotographs are produced in FIG. 3, including:

FIG. 3a—shows the 200 magnification cross-section of a slice of small intestine of a normal rat without ischemia illustrating normal, healthy villi.

Figure 3B:

FIG. 3b—shows the 100 magnification cross-section from the intestine of the placebo rat (PL) illustrating badly deteriorated villi extending from the muscle wall. The morphology is severely diminished.

Figure 3C:
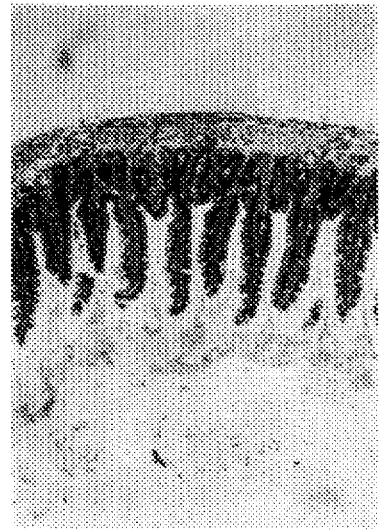

FIG. 3c—shows the 100 magnification cross-section from the intestine of the pyruvate-treated rat (PY) illustrating healthy villi. The villi retain morphology.

Thus it appears that the pyruvate treated animal maintains healthy villi and retains morphology during intestinal ischemia which is destructive of intestinal villi and reduces morphology in a similar, untreated animal.

Treatment—A patient experiencing bowel ischemia, or about to experience bowel ischemia, should receive a super physiologic dosage of pyruvate by a drip tube extended through the patient's nose to the patient's stomach, or by beverage or food containing pyruvate, or by parenteral intravenous drip. All of these delivery systems will establish the desired super physiologic level of pyruvate in the patient.

We claim:

1. A method for retarding loss of morphology in the bowel of a mammal experiencing ischemic bowel which comprises introducing a therapeutic quantity of pyruvate enterally or parenterally into the mammal prior to and during said ischemic bowel or during reperfusion.

2. The method of claim 1 wherein said pyruvate is one or more pyruvate salts or esters.

3. The method of claim 1 wherein said pyruvate is an organic ester of an amino acid.

4. The method of claim 1 wherein said pyruvate is pyruvyl alanine.

5. The method of claim 1 wherein said therapeutic quantity is from 1% to 20% by weight of the mammal's caloric intake.

6. The method of claim 1 wherein said introduction of pyruvate also retards the infiltration of neutrophils into said bowel.

7. The method of claim 1 wherein said pyruvate is introduced into said mammal during said ischemic bowel and during reperfusion.

8. A method for retarding neutrophil infiltration in the bowel of a mammal experiencing ischemic bowel which comprises introducing a therapeutic quantity of pyruvate enterally or parenterally into the mammal during said ischemic bowel or during reperfusion.

9. The method of claim 8 wherein said pyruvate is one or more pyruvate salts or esters.

10. The method of claim 8 wherein said pyruvate is an organic ester of an amino acid.

11. The method of claim 8 wherein said pyruvate is pyruvyl alanine.

12. The method of claim 8 wherein said therapeutic quantity is from 1% to 20% by weight of the mammal's caloric intake.

13. The method of claim 8 wherein said introduction of pyruvate also retards loss of morphology in said bowel.

14. The method of claim 8 wherein said pyruvate is introduced into said mammal during said ischemic bowel and during reperfusion.

* * * * *